United States Patent [19]
Wilk et al.

[11] Patent Number: 5,330,490
[45] Date of Patent: Jul. 19, 1994

[54] ENDOSCOPIC DEVICE, PROSTHESIS AND METHOD FOR USE IN ENDOVASCULAR REPAIR

[76] Inventors: Peter J. Wilk, 185 West End Ave., New York, N.Y. 10023; Jonathan Tiefenbrun, 62 Country Rd., Mamaronek, N.Y. 10543

[21] Appl. No.: 866,758
[22] Filed: Apr. 10, 1992
[51] Int. Cl.⁵ ............................................. A61B 17/00
[52] U.S. Cl. ................................. 606/153; 604/96; 623/1
[58] Field of Search ............ 623/1; 606/153, 191, 606/198; 604/96, 264

[56] References Cited

U.S. PATENT DOCUMENTS

| | | | |
|---|---|---|---|
| 4,441,495 | 4/1984 | Hicswa | 604/99 X |
| 4,733,665 | 3/1988 | Palmaz | 604/104 |
| 4,737,142 | 4/1988 | Heckele | 604/95 |
| 4,790,313 | 12/1988 | Borrelly | 604/96 X |
| 4,913,142 | 4/1990 | Kittrell et al. | 606/7 |
| 5,092,841 | 3/1992 | Spears | 604/96 |
| 5,100,429 | 3/1992 | Sinofsky et al. | 604/96 |
| 5,104,392 | 4/1992 | Kittrell et al. | 606/15 |
| 5,104,399 | 4/1992 | Lazarus | 604/96 X |
| 5,151,105 | 9/1992 | Kwan-Gett | 604/96 X |

FOREIGN PATENT DOCUMENTS

| | | |
|---|---|---|
| 9001969 | 3/1990 | PCT Int'l Appl. . |
| 9101687 | 2/1991 | PCT Int'l Appl. . |

Primary Examiner—Francis Jaworski
Attorney, Agent, or Firm—R. Neil Sudol; Henry D. Coleman

[57] ABSTRACT

In a method for performing a vascular repair operation a tubular endovascular prosthesis member made of a nontoxic biocompatible material is inserted in a collapsed configuration into a blood vessel through an incision therein. Upon insertion, the tubular prosthesis member is expanded to a cylindrical configuration and attached along its upstream and downstream edges to the vessel wall. Where the attachment is implemented via a laser, an optical fiber is inserted into the blood vessel via an angioscopic instrument having a balloon with a mouth attached about a distal end of the angioscopic insertion member so that a distal tip of the insertion member is disposed inside the balloon. The balloon is made of a material transparent to optical radiation, as well as to the wavelength of the laser beam, whereby visualization of the arterial or venous wall and the bonding of the tubular prosthesis member thereto may be implemented through the balloon. The balloon is effective to displace blood from the distal end of the endoscopic insertion member to form a transparent pocket or space, thereby enabling visual inspection of a blood vessel into which the endoscopic instrument has been inserted. Endovascular inspection may alternatively be accomplished by a combined ultrasonic and optical angioscopic instrument.

19 Claims, 4 Drawing Sheets

ENDOSCOPIC DEVICE, PROSTHESIS AND METHOD FOR USE IN ENDOVASCULAR REPAIR

BACKGROUND OF THE INVENTION

This invention relates to an endovascular technique and more particularly to a method for repairing a diseased or weakened blood vessel. This invention also relates to an endoscopic diagnostic device which, in a modified form, can be used in a surgical procedure. The endoscopic device is useful specifically, although not exclusively, in endovascular investigations and operations. This invention additionally relates to a surgical tack or staple useful, for example, in endovascular operations.

Where a vein or artery with an aneurysm or other condition has been weakened to the extent that it is in danger of rupture, corrective surgery must be performed. Such surgery conventionally entails either a bypass or a replacement of the weakened or diseased segment. In one technique, the blood vessel is dissected and laid open in the region of the weakness. A tubular prosthesis is then connected to the opened lumens on opposite sides of the dissected section.

Endovascular diagnosis and surgical operations are made difficult by the blood flow through the subject vein or artery. Although optical angioscopic instruments have been used where a vein or artery is tied off, there is alway some leakage into the vascular organ which interferes with effective visualization. Ultrasonic equipment, although useful in presenting images of endovascular structures even in the presence of substantial blood flow, does not provide the detail or wealth of information available via optical monitoring. Accordingly, endovascular surgery has been limited by the difficulty of visually monitoring endovascular structures.

OBJECTS OF THE INVENTION

An object of the present invention is to provide an endoscopic device which facilitates the diagnosis of endovascular conditions.

Another object of the present invention is to provide an endoscopic device which facilitates the execution of endovascular operations.

A further object of the present invention is to provide a method for repairing a vascular disorder such as a weakened or diseased section of an artery.

An additional object of the present invention is to provide a device for repairing a tubular organ such as a blood vessel.

Yet another object of the present invention is to provide a staple or tack useful in endovascular surgery.

SUMMARY OF THE INVENTION

A method for performing a vascular repair operation comprises, in accordance with the present invention, the steps of (a) providing a tubular member made of a nontoxic biocompatible material, (b) making an incision in a blood vessel, (c) inserting the tubular member in a collapsed configuration through the incision into the blood vessel, (d) expanding the tubular member from the collapsed configuration into an opened configuration inside the blood vessel, and (e) attaching an upstream edge of the tubular member to the blood vessel.

Pursuant to another feature of the present invention, the tubular member is bonded along the upstream edge to the blood vessel. The bonding may be implemented by a laser. In that case, an optical fiber is inserted into the blood vessel through the incision therein, a laser beam being directed at the tubular member along the upstream edge thereof. The optical fiber is preferably disposed at least partially in an angioscopic (endoscopic) instrument so that the instrument may be used to visually locate the upstream edge of the tubular member inside the blood vessel and to direct the laser beam along a desired annular locus.

According to another feature of the present invention, the endoscopic instrument for welding or bonding the upstream edge of the tubular member to the blood vessel comprises an endoscopic insertion member, an optical fiber in the endoscopic insertion member for guiding visible electromagnetic radiation to a distal end of the endoscopic insertion member, and an image transmission guide in the endoscopic insertion member for transmitting an image from the distal end to a proximal end of the endoscopic insertion member. In addition, the endoscopic instrument includes a balloon with a mouth attached about a distal end of the endoscopic insertion member so that a distal tip of the endoscopic insertion member is disposed inside the balloon. The balloon is made of a material transparent to optical radiation. An inflation channel is provided in the endoscopic insertion member for pressurizing the balloon to expand the balloon from a collapsed configuration to an expanded configuration.

The balloon is effective to displace blood from the distal end of the endoscopic insertion member to form a transparent pocket or space, thereby enabling visual inspection of a blood vessel into which the endoscopic instrument has been inserted.

The endoscopic instrument further comprises an additional optical fiber in the endoscopic insertion member for guiding a laser beam to the distal end thereof, the laser beam having a wavelength absorbable by organic tissues. The material of the balloon is also transparent to the wavelength of the laser beam, thereby enabling the beam to impinge upon the desired portions of the tubular prosthesis member while maintaining the balloon and the pocket at the distal end of the endoscopic insertion member.

It is to be noted that the balloon, besides serving to enhance the visual inspection of the artery or vein, also functions to press the upstream end of the tubular prosthesis member against the blood vessel. This function is particularly desirable where the tubular member includes an upstream portion made of graft tissue.

An annular section of graft tissue at the upstream edge of the tubular prosthesis serves in part to facilitate the attachment to the blood vessel and to generate a smooth transition zone, which reduces, if not eliminates, the chances of a clot forming at the leading edge of the tubular member.

According to another feature of the present invention, the attachment of the tubular prosthesis to the blood vessel includes the steps of (a) providing an annular reinforcement ring inside the tubular member at the upstream edge and (b) applying an annular clamping element about the blood vessel at the upstream edge to fix the blood vessel and the tubular member between the ring and the clamping element.

The reinforcement ring may be separate from the tubular member and inserted separately into the blood vessel. Alternatively, the reinforcement ring may be a rim element integral with the body of the tubular member. The annular clamping element may specifically takes the form of an elongate flexible element such as a suture, the suture being tied about the blood vessel at the upstream edge of the tubular member.

In an alternative, less preferred step, the upstream edge of the tubular prosthesis member is stapled to the blood vessel. In that event, an endoscopic or angioscopic stapling device is inserted into the blood vessel through the incision and operated to eject staples through the tubular member and the blood vessel.

According to another feature of the present invention, ultrasonic waves are generated at a point outside the blood vessel to loosen and remove hardened deposits inside the blood vessel.

Of course, the downstream edge of the tubular prosthesis may also be attached to the blood vessel.

Another endoscopic apparatus for use in visually inspecting internal body cavities comprises, in accordance with the present invention, an endoscopic insertion member, an optical fiber in the endoscopic insertion member for guiding visible electromagnetic radiation to a distal end of the endoscopic insertion member, and an image transmission guide in the endoscopic insertion member for transmitting an image from the distal end to a proximal end of the endoscopic insertion member. The apparatus further comprises an ultrasonic generator operatively connected to the endoscopic insertion member for generating an ultrasonic pressure wave at the distal end of the endoscopic insertion member, and an ultrasonic detector operatively connected to the endoscopic insertion member for sensing reflected ultrasonic waves at the distal end of the endoscopic insertion member. In addition, a video image production component is operatively connected to the image transmission guide and the ultrasonic detector for proouducing on a video monitor a video image combining structure information from both the image transmission guide and the ultrasonic detector.

Pursuant to another feature of the present invention, the video image production component includes means for filtering out images of moving fluids or fluid globules.

As discussed hereinabove, the endoscopic apparatus may further comprise (a) a balloon having a mouth attached about a distal end of the endoscopic insertion member so that a distal tip of the endoscopic insertion member is disposed inside the balloon, the balloon being made of a material transparent to optical radiation, and (b) an inflation component in the endoscopic insertion member for expanding the balloon from a collapsed configuration to an expanded configuration.

The attachment of the tubular tubular prosthesis to the inside of a blood vessel may be implemented by a surgical tack or staple comprising a shaft, an enlarged head portion attached to the shaft at one end thereof, and a plurality of barbs attached to the shaft at spaced locations therealong. The tack or staple barbs are preferably angled back towards the head portion of the tack.

A prosthesis for a tubular organ, comprises, in accordance with the present invention, a tubular member, a reinforcement ring at one end of the tubular member, the reinforcement ring being disposed inside the tubular member, and means for clamping the organ and the tubular member to the ring.

DETAILED DESCRIPTION

Figure 1A:
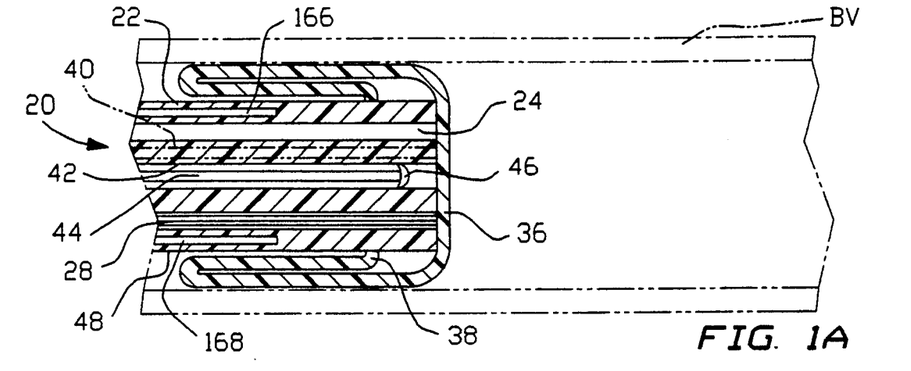
FIG. 1A is a schematic partial cross-sectional view of an endoscopic or angioscopic device in accordance with the present invention, showing a distal viewing balloon in a collapsed insertion configuration.
Figure 1B:
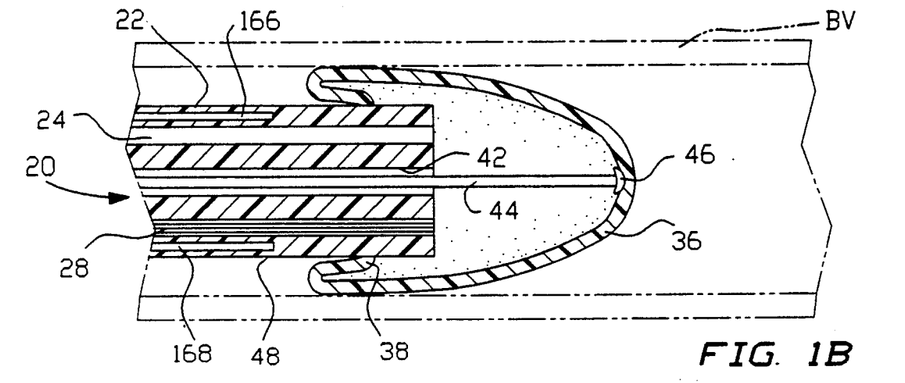
FIG. 1B is a view similar to FIG. 1A, showing the balloon in a partially expanded configuration.
Figure 1C:
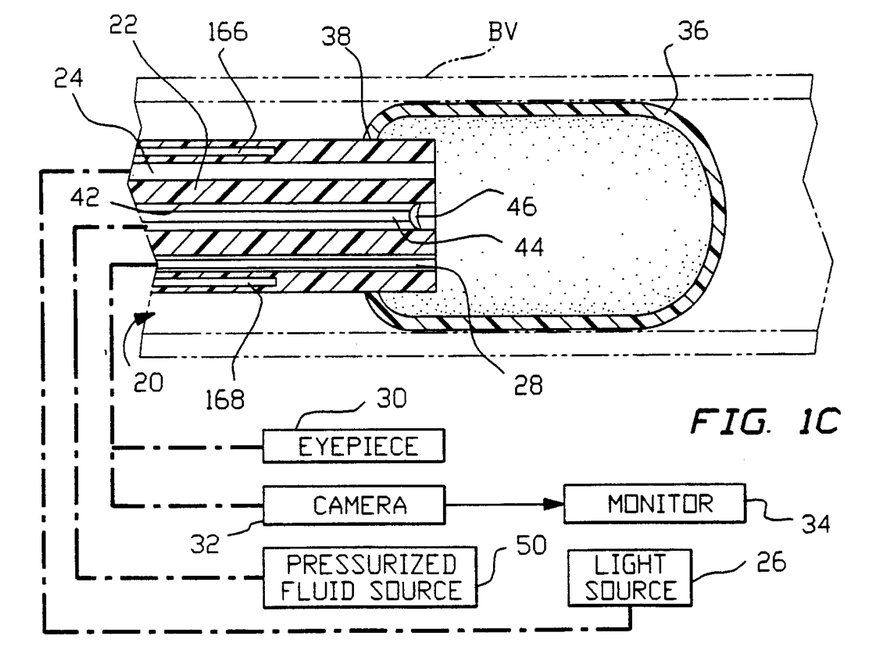
FIG. 1C is partially a partial schematic cross-sectional view and partially a block diagram of the endoscopic or angioscopic device of FIGS. 1A and 1B, showing the balloon in an expanded use configuration.

As illustrated in FIGS. 1A–1C, an endoscopic or angioscopic device 20 comprises an elongate flexible endoscopic insertion member 22. An optical fiber 24 extends longitudinally through endoscopic insertion member 22 for guiding visible electromagnetic radiation from a light source 26 (FIG. 1C) to a distal end of the endoscopic insertion member. An image transmission guide in the form of a bundle of optical fibers 28 also extends longitudinally through endoscopic insertion member 22 for transmitting an image from the distal end of the insertion member to an eyepiece 30 at a proximal end of the insertion member. Alternatively, fiber optic bundle 28 may be operatively connected to a camera 32, for example, a charge coupled device ("CCD") which in turn is connected to a video monitor 34 for displaying the image transmitted via fiber optic bundle 28. Various lenses and transparent cover plates have been omitted from the drawings for purposes of clarity.

Endoscopic device 20 further comprises a balloon 36 with a mouth 38 attached about the distal end of insertion member 22 so that a distal tip of the insertion member is disposed inside or enclosed by the balloon. Balloon 36 is made of a material transparent to optical radiation. Accordingly, objects disposed outside of balloon 36 are visible in an image transmitted over fiber optic bundle 28 to eyepiece 30 or camera 32.

Endoscopic insertion member 22 is provided with a biopsy channel 42 in which a flexible rod member 44 is slidably disposed. Rod member 44 is provided at a distal end with a headpiece or flange 46 made of a flexible material.

As illustrated in FIG. 1A, balloon 36 is initially in a collapsed configuration and is flattened back against a cylindrical outer surface 48 of endoscopic insertion member 22 during an insertion of that member in an upstream direction through an artery BV.

Upon a disposition of the distal end of insertion member 22 at a predetermined section of artery BV, rod 44 is pushed in the distal direction to shift balloon 36 out in front of the endoscopic insertion member, as illustrated in FIG. 1B. Simultaneously with or subsequently to the partial ejection of rod 44 from the distal end of endoscopic insertion member 22, a pressurized fluid source 50 (FIG. 1C) is connected to channel 42 to inflate balloon 36. The fluid from source 50 is preferably an optically transparent saline solution appropriate for intravenous feeding. In the event that balloon 36 ruptures, no undesirable air bubbles are created in the blood stream.

Balloon 36 is effective to displace blood from the distal end of endoscopic insertion member 22 to form a transparent pocket or space, thereby enabling visual inspection of a blood vessel into which the endoscopic instrument has been inserted. Upon an inflation of balloon 36 to a sufficient size, rod 44 may be retracted back into channel 42. As illustrated in FIG. 1C, headpiece or flange 46 deforms to function as a one-way valve, preventing an untimely contraction of balloon 36. To deflate balloon 36, rod is pushed partially out of channel 42.

Instead of inflating balloon 36 via biopsy channel 42, inflation may be accomplished via an auxiliary channel 40 (FIG. 1A) provided in endoscopic insertion member 22.

As discussed in detail hereinafter with reference to FIG. 9, endoscopic or angioscopic device 20 may be used also for surgical operations and not merely as a diagnostic instrument.

Figure 2:
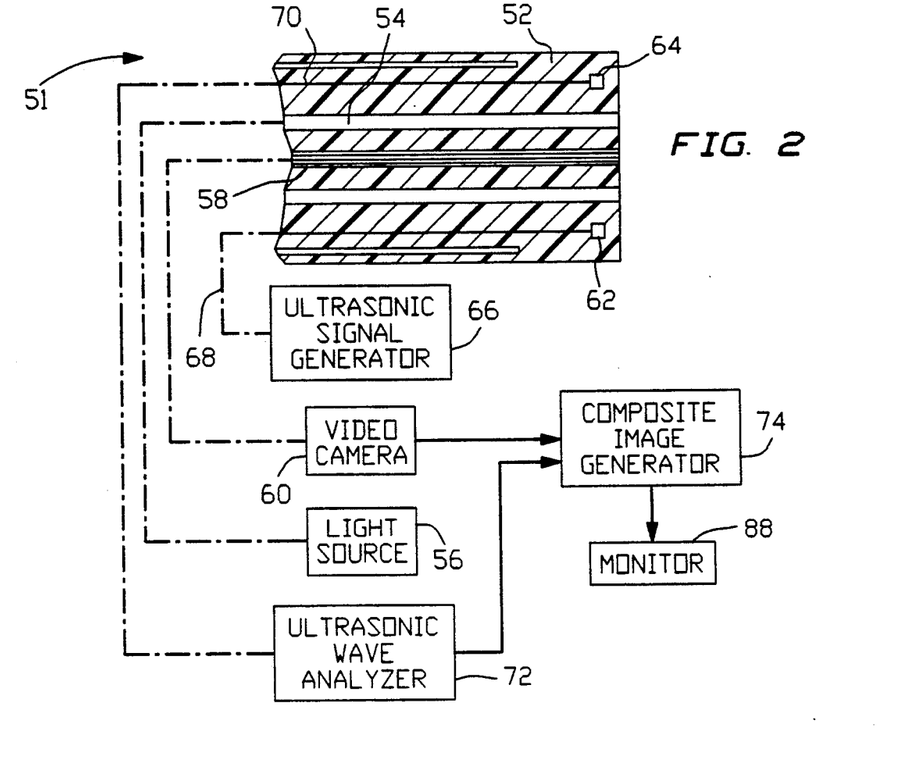
FIG. 2 is partially a partial schematic cross-sectional view and partially a block diagram of another endoscopic or angioscopic device in accordance with the present invention.

As illustrated in FIG. 2, another endoscopic device 51 for use in angioscopic diagnostic procedures comprises an elongate flexible endoscopic insertion member 52. An optical fiber 54 extends longitudinally through endoscopic insertion member 52 for guiding visible electromagnetic radiation from a light source 56 to a distal end of the endoscopic insertion member. An image transmission guide in the form of fiber optic bundle 58 also extends longitudinally through insertion member 52 for transmitting an image from the distal end of the insertion member to camera or charge coupled device ("CCD") 60 at a proximal end of the insertion member. It is to be noted that various lenses and transparent cover plates have been omitted from FIG. 2 for purposes of clarity.

Endoscopic or angioscopic device 51 further comprises a pair of transducers 62 and 64 disposed at the distal end of endoscopic insertion member 52. Transducer 62 is connected to an ultrasonic signal generator 66 via a lead 68 for producing ultrasonic pressure waves, while transducer 64 is connected via a lead 70 to an ultrasonic-wave analyzer 72. Components 62, 64, 66 and 72 are essentially standard components used in ultrasonic diagnostic equipment.

Camera 60 and analyzer 72 are operatively connected at respective outputs to a composite image generator unit 74. Unit 74 functions to combine optical image information from camera 60 with ultrasonic image information from analyzer 72 to form an enhanced image. The enhanced image includes objects which are not entirely visible or which are not visible at all with conventional optical imaging systems and which are vague or unfocused with conventional ultrasonic imaging systems. The instrument of FIG. 2 is particularly efficacious in certain endovascular diagnostic procedures or operations.

Figure 3:
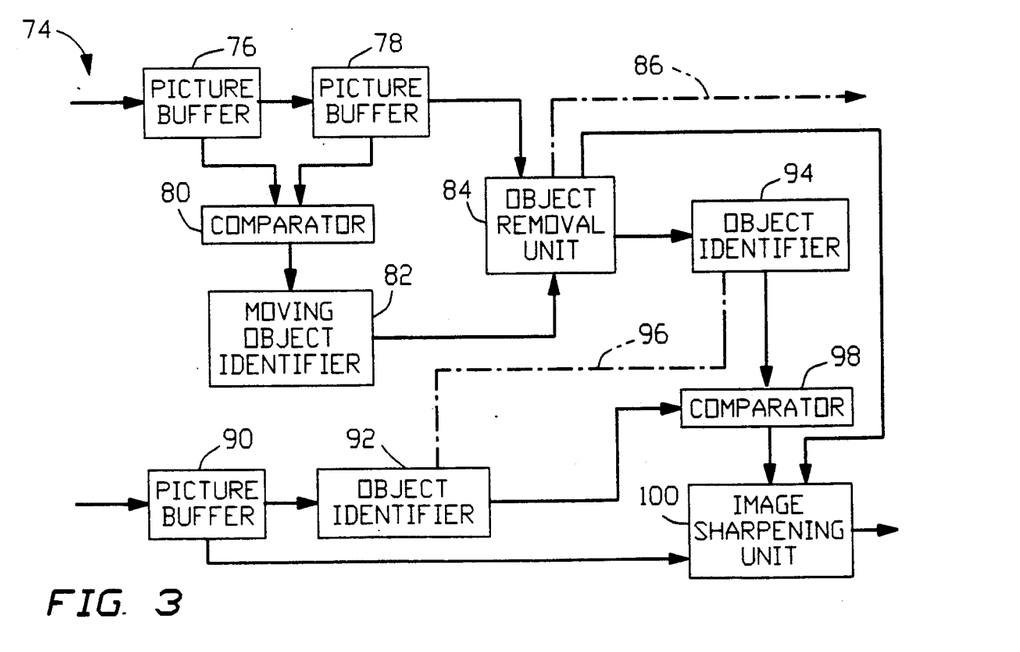
FIG. 3 is a block diagram of a composite image generator shown in FIG. 2.

As depicted in FIG. 3, composite image generator 74 includes a pair of picture buffers 76 and 78 connected in cascade to video camera 60 (FIG. 2) for storing sequential video images generated by camera 60. The sequential images in buffers 76 and 78 are analyzed by a comparator 80 and an identifier unit 82 to isolate moving elements such as globs of blood in the video field. Identifier unit 82 and picture buffer 78 are connected to a unit 84 which serves to remove the moving objects from the video image generated by camera 60. In the event that a subject vein or artery into which endoscopic insertion member 52 (FIG. 2) has been inserted has been tied off or clamped upstream, the image generated by object removal unit 84 may be sufficently clear for visual inspection by the operating surgeon. In that case, the image is transmitted from unit 84 via a lead 86 to a video monitor 88 (FIG. 2).

As further depicted in FIG. 3, composite image generator 74 includes another picture buffer 90 operatively connected to ultrasonic wave analyzer 72 for temporarily storing images produced thereby. An object identifier unit 92 at an output of buffer or register 90 operates to define different parts of an ultrasonically derived image in the buffer. Another object identifier unit 94 at an output of object removal unit 84 operates to define different parts of an optically derived image transmitted over the output to identifier unit 94. Identifier units 92 and 94 are synchronized, as schematically represented by dot-dash connection 96, and are tied to a video comparator 98 which functions to match the different objects in the optically derived image with the corresponding objects in the ultrasnonically derived image. Comparator 98 is connected at an output to an image sharpening unit 100 for controlling the operation thereof. Image sharpening unit 100 receives optically derived video images from object removal unit 84 and corresponding ultrasonically derived images from picture buffer 90 and, in response to signals from comparator 98, replaces selected objects in the images from buffer 90 with the corresponding optical images from unit 84.

Other circuits for combining ultrasonically derived images and optically derived images will be apparent to one skilled in the art of image processing.

Figure 4:
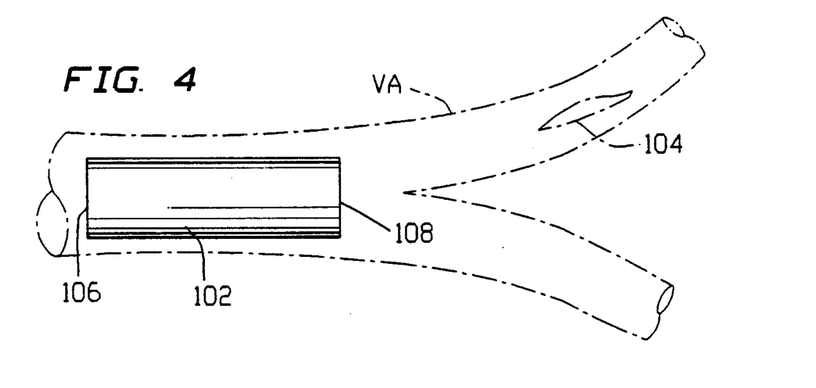
FIG. 4 is a side elevational view, on an enlarged scale, of a tubular endosvascular prosthesis, in accordance with the present invention, showing placement of the prosthesis in an artery to repair a weakened section of the arterial wall.

As illustrated in FIG. 4, in performing an endovascular repair operation, a tubular prosthesis member 102 made of a non-toxic biocompatible material is positioned inside a vein or artery VA at a weakened or malfunctioning segment thereof. The segment may, for example, be the site of an aneurysm (not illustrated). Tubular prosthesis member 102 has a limited flexibility, whereby the member may be temporarily collapsed or folded for insertion into vessel VA through an incision 104 made therein. Tubular member 102 may be made of a shape memory substance which has a tubular configuration at temperatures approaching 98.6° F. but which assumes or can assume a collapsed or folded configuration at lower temperatures, for example, at room temperature.

Upon insertion into vessel VA, tubular prosthesis member 102 is expanded or allowed to expand from the collapsed configuration into an opened configuration. An upstream edge 106 of tubular member 102 is then attached to blood vessel VA. Preferably, a downstream edge 108 of tubular prosthesis member 102 is also attached to vessel VA. This attaching of the tubular prosthesis member to vessel VA may be implemented by any of a number of equivalent techniques, such as stapling, ultrasonic or laser welding or tying. Some of these techniques are described in detail hereinafter with reference to FIGS. 5-12.

Figure 5:
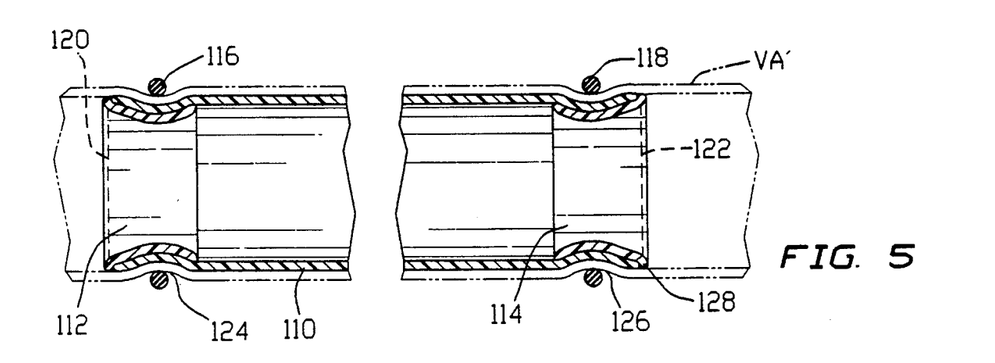
FIG. 5 is a schematic longitudinal cross-sectional view, on an enlarged scale, of a specific embodiment of a tubular endosvascular prosthesis in accordance with the present invention.

As illustrated in FIG. 5, a tubular endovascular prosthesis 110 may be attached to a vessel VA' via a pair of rings 112 and 114 also inserted into the vessel via an incision (not illustrated). Tubular prosthesis member 110 and rings 112 and 114 are made of a nontoxic biocompatible material which has a limited flexibility, whereby the tubular member and the rings may be temporarily collapsed or folded for insertion into vessel VA'. Tubular prosthesis member 110 and rings 112 and 114 may be made of a shape memory substance which has an annular configuration at temperatures approaching 98.6° F. but which assumes or can assume a collapsed or folded configuration at lower temperatures, for example, at room temperature. Alternatively, tubular prosthesis member 110 and rings 112 and 114 may be made of a polymeric substance which is fairly rigid but which can be collapsed upon the application of sufficient pressure.

Rings 112 and 114 are disposed inside tubular prosthesis member 110 and cofunction with respective ties 116 and 118 to respectively fix a downstream edge 120 and an upstream edge 122 of tubular prosthesis member 110 to blood vessel VA'. To that end, rings 112 and 114 may be provided along their outer sides with annular grooves 124 and 126 for partially receiving ties 116 and 118. In addition, at least upstream ring 114 may be formed with an outwardly turned lip 128 for digging into blood vessel VA' and thereby forming a smooth or continuous surface therewith. Rings 112 and 114 are thus formed to minimize dead spots in the flow of blood which might lead to clotting.

Figure 6:
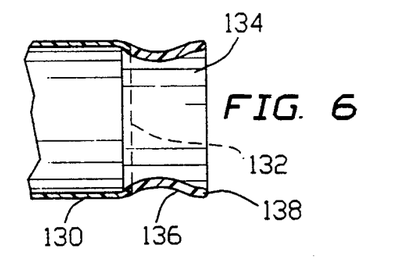
FIG. 6 is a partial schematic longitudinal cross-sectional view, on an enlarged scale, of another specific embodiment of a tubular endosvascular prosthesis in accordance with the present invention.

As shown in FIG. 6, another tubular prosthesis member 130 is pre-attached at an upstream edge 132 to a reinforcement ring 134 having an annular outer groove 136 and an outwardly turned leading lip 138. Tubular member 130 and ring 134 are thus inserted together into a vein or artery through an incision therein.

Figure 7:
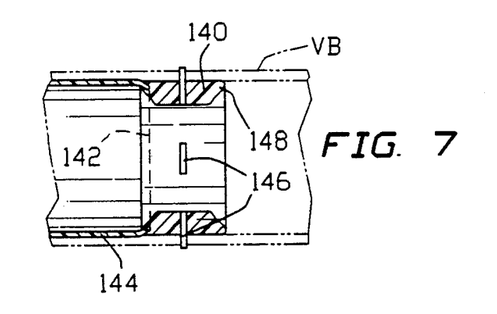
FIG. 7 is a partial schematic longitudinal cross-sectional view, on an enlarged scale, of an additional embodiment of a tubular endosvascular prosthesis in accordance with the present invention.

As depicted in FIG. 7, a ring 140 at a leading edge 142 of a tubular endovascular prosthesis member 144 may be attached to a blood vessel VB via a plurality of staples or tacks 146. As described hereinabove with reference to FIG. 5, ring 142 may be formed along an upstream side with an outwardly turned lip 148 for forming a smooth interface with the inner surface of blood vessel VB.

Figure 8:
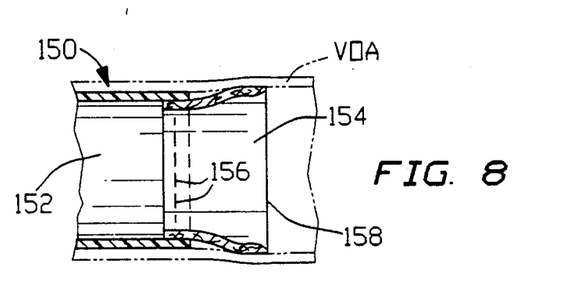
FIG. 8 is a partial schematic longitudinal cross-sectional view, on an enlarged scale, of yet another embodiment of a tubular endosvascular prosthesis in accordance with the present invention.

Yet another endovascular prosthesis member 150 is illustrated in FIG. 8. Prosthesis member 150 includes a tubular body member 152 and an annular graft portion 154 attached to the tubular member 152 along a leading or upstream edge 154 thereof, for example, via sutures 156. An annular leading edge 158 of graft portion 154 is bonded to a vein or artery VOA via a laser technique or by ultrasonic welding or cauterization.

Figure 9:
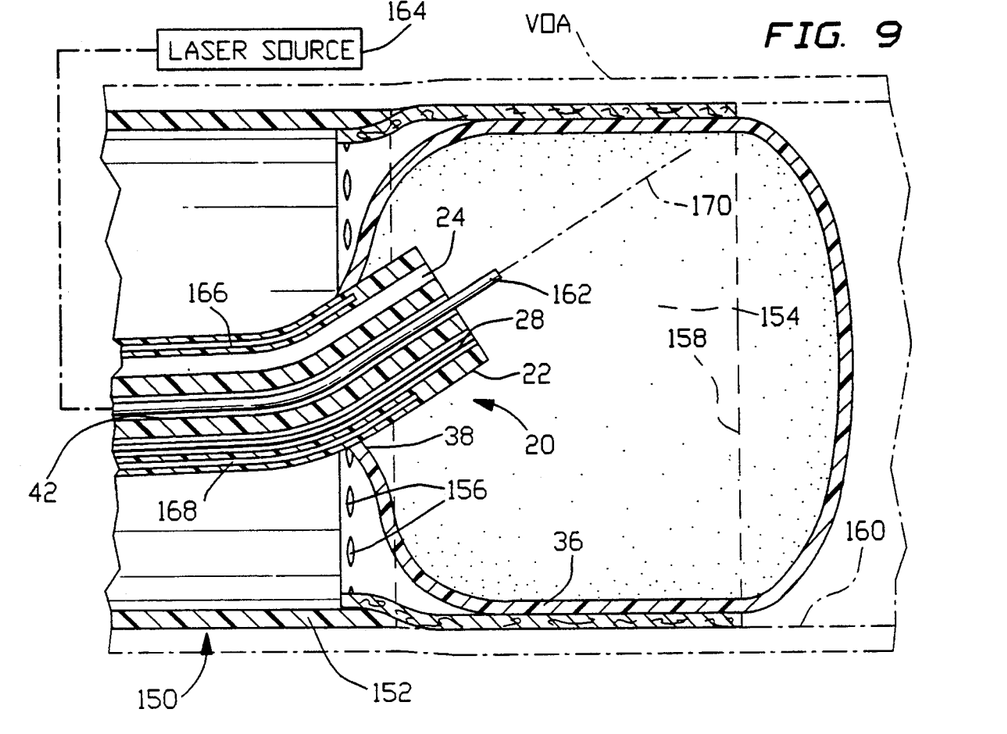
FIG. 9 is a schematic partial cross-sectional view of the endoscopic device of FIGS. 1A-1C and the tubular endovascular prosthesis of FIG. 8, showing use of the endoscopic device to attach the prosthesis to a blood vessel.

FIG. 9 illustrates the use of endoscopic or angioscopic device 20 (FIGS. 1A-1C) to attach endovascular prosthesis 150 (FIG. 8) to vein or artery VOA. Upon a positioning of prosthesis 150 inside vein or artery VOA, endoscopic insertion member 22 of endoscopic or angioscopic device 20 is inserted into the vein or artery. As described hereinabove with reference to FIGS. 1B and 1C, balloon 36 is inflated to press annular graft portion 154 against an inner surface 160 of vein or artery VOA. Balloon 36 facilitates the visual inspection of the graft portion 154 to determine that it has been properly positioned.

Upon the inflation of balloon 36, rod 44 is removed from channel 42, balloon 36 being maintained in an inflated configuration. An optical fiber 162 connected to a laser source 164 is then inserted through channel 42. Tensioning cables 166 and 168 inside endoscopic insertion member 22 are selectively placed under tension to control the direction in which the distal end portion of endoscopic insertion member 22 is turned, thereby controlling the direction of a laser beam 170 from optical fiber 162. As in FIGS. 1A-1C, lenses and other elements of the endoscopic insertion member 22 have been omitted from the schematic representation of FIG. 9 for purposes of clarity.

It is to be noted that laser beam 170 has a wavelength absorbable by vascular tissues. The material of balloon 36 is transparent to the wavelength of laser beam 170, thereby enabling the beam to impinge upon the desired portions of annular graft portion or collar 154 while maintaining balloon 36 and the fluid filled pocket at the distal end of the endoscopic insertion member.

Figure 10:
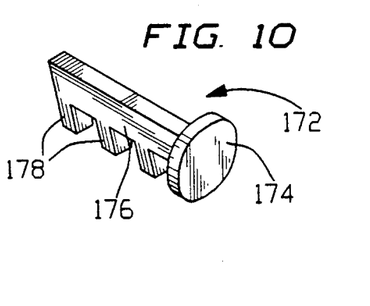
FIG. 10 is a perspective view of a staple or tack for use in endovascular surgery.
Figure 11:
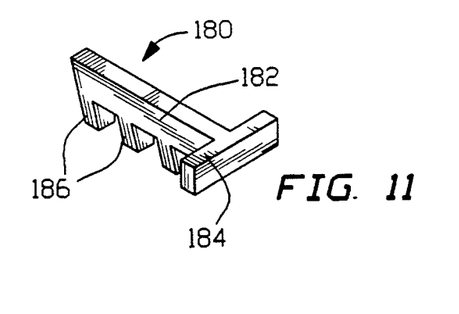
FIG. 11 is a perspective view of another staple or tack for use in endovascular surgery.

FIG. 10 is a perspective view of a staple or tack 172 for use in endovascular surgery. Tack 172 has a semispherical or disk-shaped head portion 174 connected to a shaft 176 at one end thereof and a plurality of rearwardly angled barbs 178 projecting from the shaft 176 at spaced intervals therealong. Another tack 180 has a shaft 182 and a head bar 184 connected to one another in a T shape. Shaft 182 is provided with a plurality of rearwardly angled barbs 186 projecting from the shaft at spaced intervals therealong.

Figure 12:
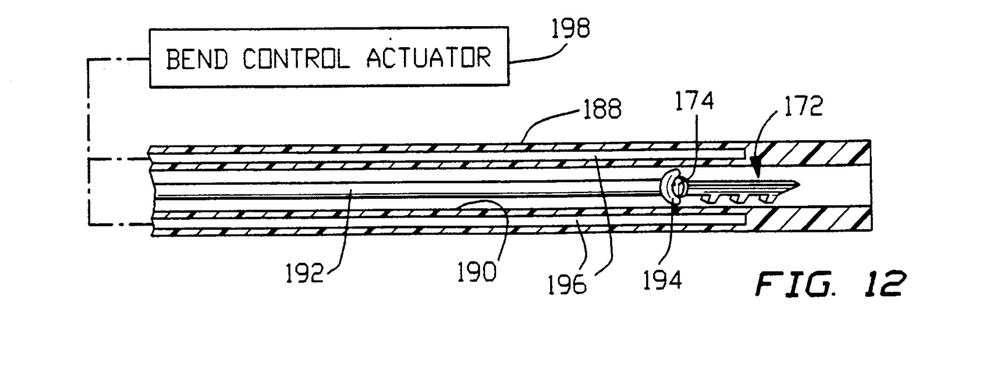
FIG. 12 is a schematic partial cross-sectional view of a tack applicator device insertable through the biopsy channel of an endoscopic or angioscopic device to apply a tack endovascularly.

As illustrated in FIG. 12, a device for applying tack 172 or 180 comprises a flexible elongate tubular body member 188 having a channel 190 through which an ejector rod 192 is slidably inserted. At a distal end, rod 192 has a seat 194 for receiving head portion 174 or head bar 184. Barbs 178 or 186 are flexible and can be bent towards the respective tack shaft 176 or 182 upon insertion of the tack into channel 190.

Tubular body member 188 is insertable through the biopsy channel of an endoscopic or angioscopic device, e.g., channel 42 of endoscopic or angioscopic device 20, to apply tack 172 or 180 endovascularly. To that end, tubular body member 188 is pushed in the distal direction through channel 42 (FIGS. 1A-1C) so that the distal tip of the applicator body member 188 engages tissues to be stapled. At that juncture, rod 192 is pushed in the distal direction through channel 190 to eject tack 172 or 180 and to press the tack through the tubular prosthesis member and the blood vessel which are to be attached to one another, as described hereinabove. Upon the application of a tack, rod 192 is removed for inserting another tack.

The tack applicator device of FIG. 12 may be provided with a plurality of tensioning wires 196 which extend longitudinally through tubular body member 188 and which are operatively connected at their proximal ends to a bend control actuator 198, which may be a mechanical knob, or a joystick or roller ball ("mouse") assembly. Operation of bend control actuator 198 controls the orientation of a distal end portion of the tack applicator. Similar directional controls may be provided on optical fiber 162 (FIG. 9).

Prior to the installation of a tubular endovascular prosthesis member as described herein, any plaque or calcified deposits on the inside of the arterial or venous segment being repaired may be broken up by ultrasonic waves directed at the arterial or venous segment through the wall thereof, i.e., from the body cavity.

Although the invention has been described in terms of particular embodiments and applications, one of ordinary skill in the art, in light of this teaching, can generate additional embodiments and modifications without departing from the spirit of or exceeding the scope of the claimed invention. For example, a tubular prosthesis member may be used in other tubular organs such as the intestines, attachment of the tubular member to the tubular organ being effectuated as described hereinabove for a blood vessel.

In additional, a tubular prosthesis member may be made entirely of graft tissue, instead of synthetic material as discussed above.

Accordingly, it is to be understood that the drawings and descriptions herein are proferred by way of example to facilitate comprehension of the invention and should not be construed to limit the scope thereof.

What is claimed is:

1. A method for performing a vascular repair operation, comprising the steps of:
   providing a tubular member made of a nontoxic biocompatible material;
   making an incision in a blood vessel;
   inserting said tubular member in a collapsed configuration through said incision into said blood vessel;
   expanding said tubular member from said collapsed configuration into an opened configuration inside said blood vessel; and
   bonding an upstream edge of said tubular member to said blood vessel by inserting an optical fiber through said incision into said blood vessel and directing a laser beam at said tubular member along said upstream edge, said optical fiber being disposed at least partially in an angioscopic instrument, further comprising the step of using said angioscopic instrument to locate said upstream edge inside said blood vessel.

2. The method defined in claim 1 wherein said angioscopic instrument includes a balloon having a mouth attached about a distal end of said angioscopic instrument so that a distal tip of said angioscopic instrument is disposed inside said balloon, said balloon being made of a material transparent to both optical radiation and the wavelength of said laser beam, further comprising the steps of inflating said balloon at least partially inside said tubular member in a region about said upstream edge and directing said laser beam at said upstream edge through said balloon.

3. The method defined in claim 1, further comprising the step of attaching a downstream edge of said tubular member to said blood vessel.

4. The method defined in claim 1 wherein said tubular member has an upstream portion formed of graft tissue which defines said upstream edge.

5. A method for performing a vascular repair operation, comprising the steps of:
   providing a tubular member made of a nontoxic biocompatible material;
   making an incision in a blood vessel;
   inserting said tubular member in a collapsed configuration through said incision into said blood vessel;
   expanding said tubular member from said collapsed configuration into an opened configuration inside said blood vessel; and
   attaching an upstream edge of said tubular member to said blood vessel, said step of attaching including the steps of (a) providing an annular reinforcement ring inside said tubular member at said upstream edge and (b) applying an annular clamping element about said blood vessel at said upstream edge to fix said blood vessel and said tubular member between said ring and said clamping element.

6. The method defined in claim 5 wherein said reinforcement ring is separate from said tubular member and is inserted separately into said blood vessel.

7. The method defined in claim 5 wherein said annular clamping element takes the form of an elongate flexible element, said step of applying including the step of tying said flexible element about said blood vessel at said upstream edge of said tubular member.

8. A method for performing a vascular repair operation, comprising the steps of:
   providing a tubular member made of a nontoxic biocompatible material;
   making an incision in a blood vessel;
   inserting said tubular member in a collapsed configuration through said incision into said blood vessel;
   expanding said tubular member from said collapsed configuration into an opened configuration inside said blood vessel;
   inserting an angioscopic instrument through said incision into said blood vessel;
   using said angioscopic instrument to locate an upstream edge of said tubular member inside said blood vessel; and
   upon locating said upstream edge by using said angioscopic instrument, inserting attaching an upstream edge of said tubular member to said blood vessel.

9. The method defined in claim 8 wherein said step of attaching includes the steps of stapling said upstream edge to said blood vessel.

10. The method defined in claim 9 wherein said step of attaching includes the step of inserting a stapling device into said blood vessel through said incision and operating said stapling device to eject staples through said tubular member and said blood vessel.

11. The method defined in claim 8 wherein said step of attaching includes the step of bonding said tubular member along said upstream edge to said blood vessel.

12. The method defined in claim 11 wherein said step of bonding includes the steps of inserting an optical fiber through said incision into said blood vessel and directing a laser beam at said tubular member along said upstream edge.

13. The method defined in claim 8 wherein said angioscopic instrument includes a balloon having a mouth attached about a distal end of said angioscopic instrument so that a distal tip of said angioscopic instrument is disposed inside said balloon, said balloon being made of a material transparent to both optical radiation and the wavelength of said laser beam, further comprising the steps of inflating said balloon at least partially inside said tubular member in a region about said upstream edge and directing said laser beam at said upstream edge through said balloon.

14. The method defined in claim 8 wherein said step of attaching includes the steps of (a) providing an annular reinforcement ring inside said tubular member at said upstream edge and (b) applying an annular clamping element about said blood vessel at said upstream edge to fix said blood vessel and said tubular member between said ring and said clamping element.

15. The method defined in claim 14 wherein said reinforcement ring is separate from said tubular member and is inserted separately into said blood vessel.

16. The method defined in claim 14 wherein said annular clamping element takes the form of an elongate flexible element, said step of applying including the step of tying said flexible element about said blood vessel at said upstream edge of said tubular member.

17. The method defined in claim 8 wherein said step of attaching includes the step of stapling said upstream edge to said blood vessel.

18. The method defined in claim 17 wherein said step of attaching includes the step of inserting a stapling device into said blood vessel through said incision and operating said stapling device to eject staples through said tubular member and said blood vessel.

19. The method defined in claim 8, further comprising the step of attaching a downstream edge of said tubular member to said blood vessel.

* * * * *

UNITED STATES PATENT AND TRADEMARK OFFICE
CERTIFICATE OF CORRECTION

PATENT NO. : 5,330,490
DATED : July 19, 1994
INVENTOR(S) : Peter J. Wilk and Jonathan Tiefenbrun It is certified that error appears in the above-indentified patent and that said Letters Patent is hereby corrected as shown below:

```
     Column 3, line 2, change "takes" to --take--;
line 36, change "prooduc-" to --produc---;
line 56, delete "tubular" (second occurrence).

Column 10, line 51, delete "inserting".
```

Signed and Sealed this

Seventh Day of November, 1995

Attest:

BRUCE LEHMAN

*Attesting Officer*   *Commissioner of Patents and Trademarks*